(12) United States Patent
Huang

(10) Patent No.: US 11,892,709 B2
(45) Date of Patent: Feb. 6, 2024

(54) FRAGRANT EYEGLASSES

(71) Applicant: AD GLOBAL CO., LTD., Tainan (TW)

(72) Inventor: Chih-Chang Huang, Tainan (TW)

(73) Assignee: AD GLOBAL CO., LTD., Tainan (TW)

( * ) Notice: Subject to any disclaimer, the term of this patent is extended or adjusted under 35 U.S.C. 154(b) by 265 days.

(21) Appl. No.: 17/395,792

(22) Filed: Aug. 6, 2021

(65) Prior Publication Data
US 2023/0043309 A1    Feb. 9, 2023

(51) Int. Cl.
*G02C 11/00*   (2006.01)
*G02C 5/12*    (2006.01)
*A61L 9/12*    (2006.01)

(52) U.S. Cl.
CPC .............. *G02C 11/00* (2013.01); *A61L 9/12* (2013.01); *G02C 5/12* (2013.01)

(58) Field of Classification Search
CPC .......... G02C 11/00; G02C 5/12; G02C 5/126; A61L 9/12
See application file for complete search history.

(56) References Cited

U.S. PATENT DOCUMENTS

| | | | | |
|---|---|---|---|---|
| 4,813,776 A * | 3/1989 | Borsos | ............... | G02C 5/126 351/137 |
| 5,233,371 A * | 8/1993 | Guillet | ............... | G02C 11/00 351/158 |
| 5,636,787 A * | 6/1997 | Gowhari | ............ | A61M 15/085 239/36 |
| 6,312,125 B1 * | 11/2001 | Potts | ...................... | G02C 11/12 351/158 |
| 2005/0162610 A1 * | 7/2005 | Kim | ......................... | G02C 9/04 351/47 |
| 2009/0216070 A1 * | 8/2009 | Hunt | ...................... | A61M 21/02 463/31 |
| 2018/0104516 A1 * | 4/2018 | Fegan | ..................... | G02C 5/12 |
| 2020/0355936 A1 * | 11/2020 | De La Fuente | ........ | G02C 11/00 |
| 2022/0026744 A1 * | 1/2022 | Hutchins | ................ | A61L 9/014 |

FOREIGN PATENT DOCUMENTS

| CN | 104656279 A | * | 5/2015 |
| CN | 204595355 U | * | 8/2015 |
| CN | 107102451 A | * | 8/2017 |

(Continued)

*Primary Examiner* — Christopher Stanford
(74) *Attorney, Agent, or Firm* — Rosenberg, Klein & Lee

(57) ABSTRACT

A type of fragrant eyeglasses is revealed. The fragrant eyeglasses include an eyeglass body and a nose bridge which is arranged at the eyeglass body and provided with a mounting space for mounting fragrance tablets. At least one air inlet and at least one air outlet for guiding air flows are disposed on a front side and a rear side of the mounting space respectively. Thereby the fragrance tablet mounted in the nose bridge is just adjacent to the user's nose when the eyeglasses are fitted on bridge of user's nose by the nose bridge. Thus the user smells scents emanated from the fragrance tablet and feels refreshing and soothing. The air inlet and the air outlet not only help emanation of scents from the fragrance tablet, but also guide the scents to spread along with air flows induced by movements of people who while walking or riding bicycles.

2 Claims, 7 Drawing Sheets

(56) References Cited

FOREIGN PATENT DOCUMENTS

| CN | 208156337 U | * | 11/2018 | |
|---|---|---|---|---|
| DE | 3921987 A1 | * | 1/1991 | |
| JP | H11271689 A | * | 10/1999 | |
| JP | 2005091851 A | * | 4/2005 | |
| JP | 2007020975 A | * | 2/2007 | |
| KR | 200364065 Y1 | * | 10/2004 | |
| KR | 200390668 Y1 | * | 7/2005 | |
| KR | 200460042 Y1 | * | 4/2012 | |
| KR | 101277263 B1 | * | 6/2013 | |
| KR | 20150007453 A | * | 1/2015 | |
| KR | 101571448 B1 | * | 11/2015 | |
| WO | WO-2008155586 A1 | * | 12/2008 | ............. A45D 34/02 |

* cited by examiner

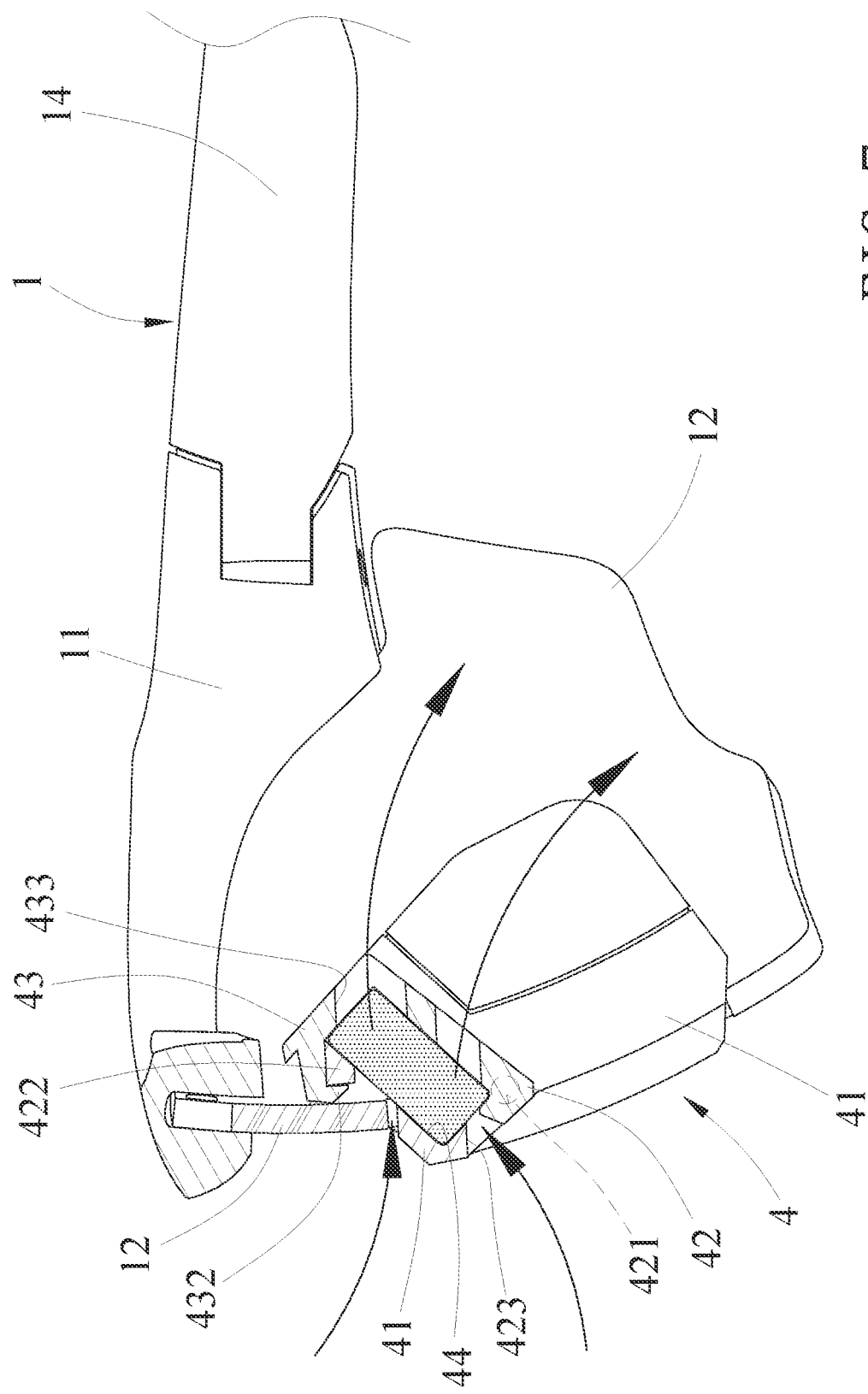

FRAGRANT EYEGLASSES

BACKGROUND OF THE INVENTION

Field of the Invention

The present invention relates to eyeglasses, especially to fragrant eyeglasses in which at least one fragrant tablet is arranged at a nose bridge of the eyeglasses for allowing users to smell scents emanated from the fragrant tablet easily.

Description of Related Art

Besides practical functions such as vision correction, eye protection, etc., eyeglasses also need to have pleasing appearance and visual aesthetics. However, the eyeglasses provide no sense of smell. Perfume has become one of modern people's daily necessities and its scents not only relieve fatigue and nervous stress but also make people joyful and relaxed. The perfume available now is sprayed on skin or clothes so that the scent is easily lost in a short time and some people with sensitive skin may have allergies. Once the points where the perfume is applied are far away from user's face or nose, the user can't smell the scent of the perfume easily. As to the eyeglasses, the user needs to wear them on the nose and face for a long time. If the eyeglasses can release a fresh scent, users can feel fresh and comfortable while wearing them.

SUMMARY OF THE INVENTION

Therefore, it is a primary object of the present invention to provide a type of fragrant eyeglasses in which at least one fragrant tablet is arranged at a nose bridge of eyeglasses for allowing users to smell scents emanated from the fragrant tablet easily.

In order to achieve the above object, a type of fragrant eyeglasses according to the present invention includes an eyeglass body provided with a nose bridge which has a mounting space for mounting at least one fragrance tablet. At least one air inlet and at least one air outlet for guiding air flows are disposed on a front side and a rear side of the mounting space respectively. When the present eyeglasses are fitted on bridge of the nose by the nose bridge, the fragrance tablet mounted in the nose bridge is just adjacent to the nose so that the user smells scents emanated from the fragrance tablet during breathing and feels refreshing and more energetic. The air inlet and the air outlet not only help the emanation of the scents from the fragrance tablet, but also guide the scents from the fragrance tablet to spread along with air flows created by the users who are walking or riding bikes. Thereby the users smell the scents easier to revitalize their minds and bodies.

BRIEF DESCRIPTION OF THE DRAWINGS

The structure and the technical means adopted by the present invention to achieve the above and other objects can be best understood by referring to the following detailed description of the preferred embodiments and the accompanying drawings, wherein:

FIG. 7 is a partial enlarged sectional view of another embodiment according to the present invention.

DETAILED DESCRIPTION OF THE PREFERRED EMBODIMENT

Refer to FIGS. 1-4, a type of fragrant eyeglasses according to the present invention includes an eyeglass body 1, a nose bridge 2, and at least one fragrance tablet 3.

Figure 1:
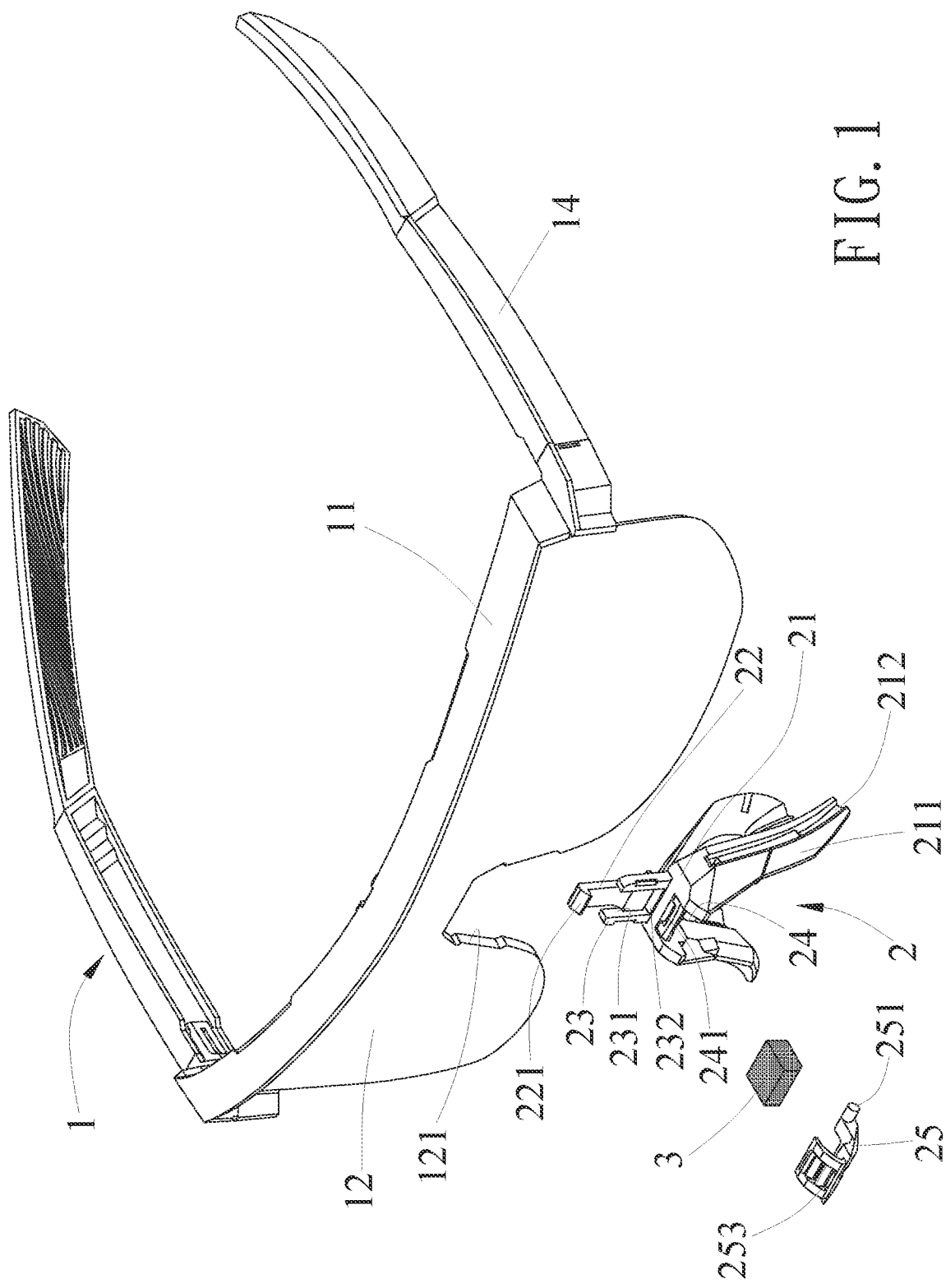
FIG. 1 is an exploded view of an embodiment according to the present invention.
Figure 2:
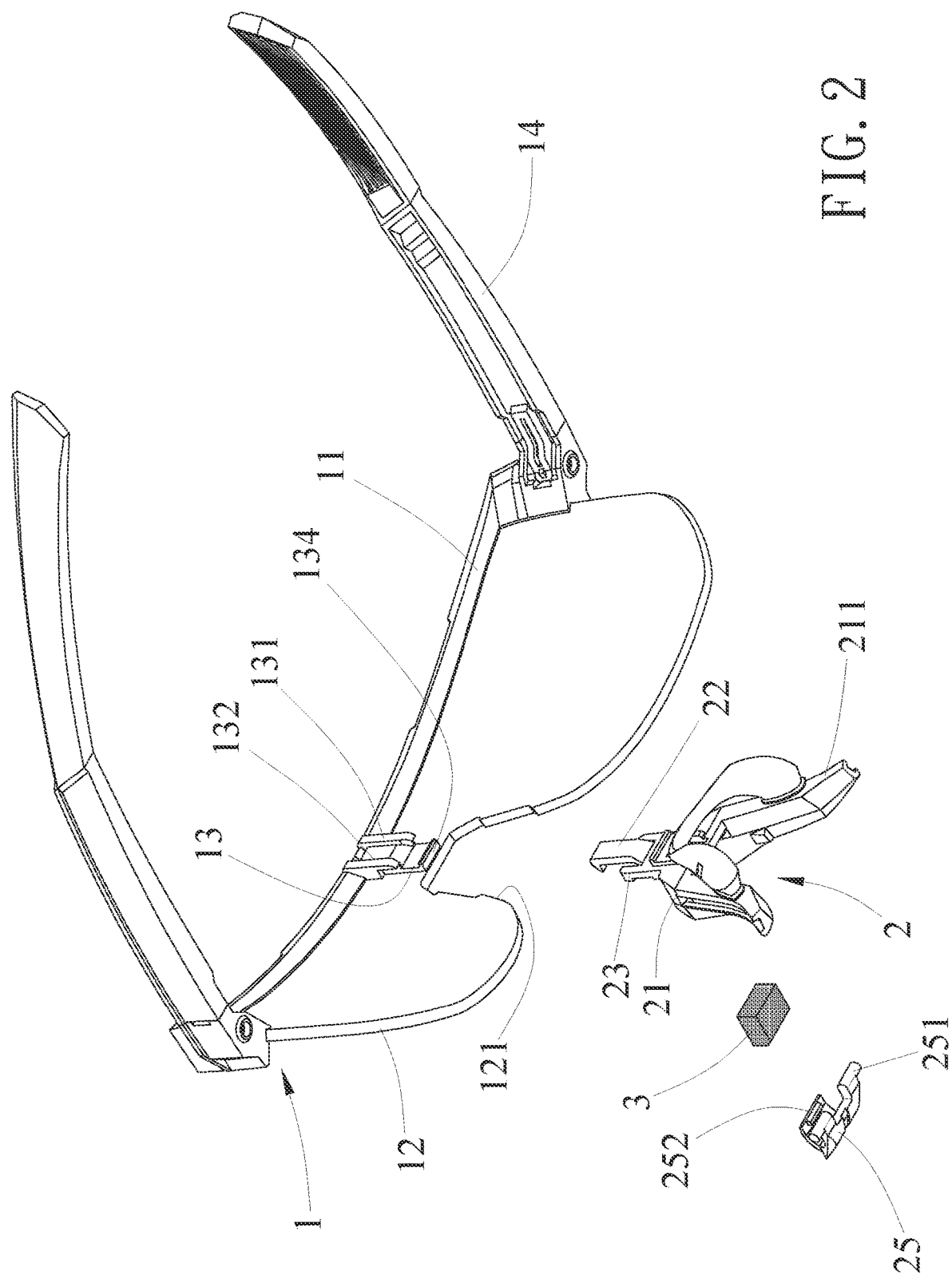
FIG. 2 is another exploded view of an embodiment according to the present invention.
Figure 3:
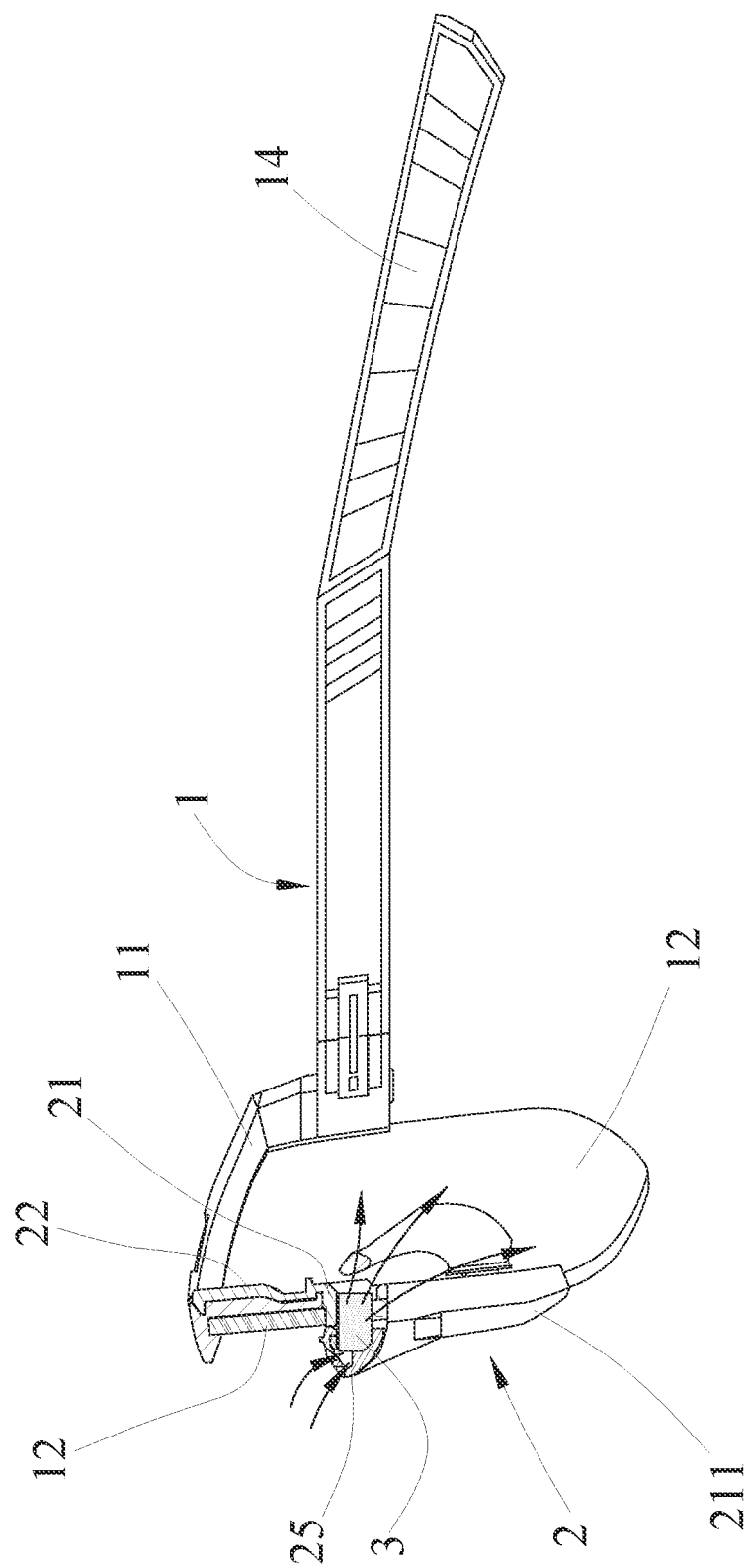
FIG. 3 is a sectional view of an embodiment according to the present invention.
Figure 4:
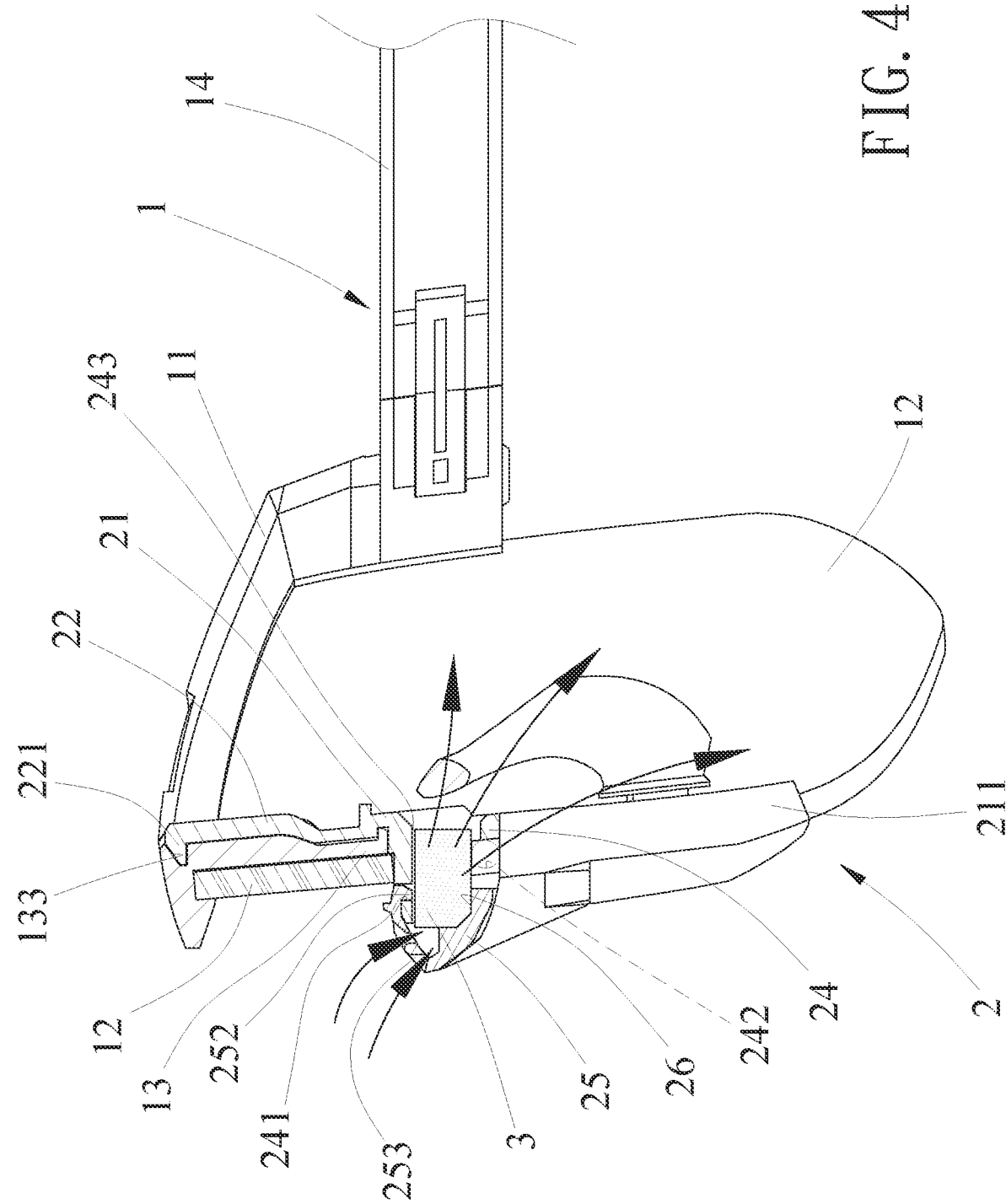
FIG. 4 is a partial enlarged sectional view of another embodiment according to the present invention.

The eyeglass body 1 consists of a frame 11 having a front surface and a rear surface opposite to each other, a lens 12 disposed on the frame 11, a nose-bridge assembly portion 13 arranged at the rear surface of the frame 11, and two temples 14 arranged at left and right sides of the frame 11 correspondingly. An inverted V-shaped notch 121 is formed on a middle portion of a bottom side of the lens 12. As shown in FIG. 2 and FIG. 4, the nose-bridge assembly portion 13 is composed of two positioning pieces 131 on left and right sides thereof, a positioning area 132 formed between the two positioning pieces 131, a first locking slot 133 arranged at an upper end of the positioning area 132, and a second tenon 134 disposed on a lower end of the positioning area 132.

The nose bridge 2 is composed of a bridge body 21, a connection piece 22, a limiting piece 23 formed on each of two sides of a front surface of the connection piece 22, a fixing-piece assembly portion 24, a fixing piece 25 located in front of the fixing-piece assembly portion 24, and a mounting space 26 formed between the fixing-piece assembly portion 24 and the fixing piece 25. A wing portion 211 is formed on each of two sides of the bridge body 21 and provided with a mounting slot 212 which is mounted and connected to the notch 121 of the lens 12. The connection piece 22 is formed above the two wing portions 211 of the bridge body 21 for being mounted to the positioning area 132 of the nose-bridge assembly portion 13 on the frame 11. A first tenon 221 is formed on an upper end of the connection piece 22 for being locked and positioned in the first locking slot 133 on an upper end of the nose-bridge assembly portion 13. A limit area 231 is formed between the two limiting pieces 23 and used for mounting the two positioning pieces 131 on the frame 11 therein while a second locking slot 232 is formed under the limit area 231 for being locked and positioned by the second tenon 134 on a lower end of the nose-bridge assembly portion 13 at the frame 11. The fixing-piece assembly portion 24 is formed between the two wing portions 211 of the bridge body 21 and provided with a locking hole 241 on a top end thereof and two pivot holes 242 on left and the right sides thereof. The fixing piece 25 includes a pivot pin 251 disposed on each of two sides thereof, a locking block 252 formed on an upper end thereof, and at least one air inlet 253 corresponding to the mounting space 26. The pivot pin 251 is pivotally connected to the pivot hole 242 of the fixing-piece assembly portion 24 while the locking block 252 is mounted and locked in the locking hole 241 on the top end of the fixing-piece assembly portion 24. The fixing-piece assembly portion 24 is further provided with at least one air outlet 243 corresponding to the mounting space 26 while both the air outlet 243 and the air inlet 253 are aligned with each other and communicated with the mounting space 26.

The fragrance tablet 3 is mounted in the mounting space 26 of the nose bridge 2 and provided with essential oil attached thereto.

While in use, the locking block 252 on the upper end of the fixing piece 25 and the locking hole 241 on the top end of the fixing-piece assembly portion 24 of the nose bridge 2 are released from the locked state. Then the fragrance tablet 3 is mounted into the mounting space 26 formed between the fixing-piece assembly portion 24 and the fixing piece 25. Next the locking block 252 of the fixing piece 25 is locked into the locking hole 241 on the top end of the fixing-piece assembly portion 24 again so that the fragrance tablet 3 is mounted and fixed in the mounting space 26 of the nose bridge 2.

When users wear the present eyeglasses, the nose bridge 2 is arranged on the nose of the user by the wing portions 211 on two sides thereof and the fragrance tablet 3 in the nose bridge 2 is just located adjacent to the user's nose. Thus users can smell scents emanated from the fragrance tablet 3 and thus feel refreshing and even relieve from fatigue. Moreover, the fixing-piece assembly portion 24 and the fixing piece 25 of the nose bridge 2 are provided with the air outlet 243 and the air inlet 253 respectively at the position corresponding to the mounting space 26. Such arrangement not only helps scented emanation of the fragrance tablet 3 but also allows users to smell the scents emanated from the fragrance tablet 3 easier while there are air flows created by users who are walking, riding bikes, etc. The air flows flow into the mounting space 26 through the air inlet 253 of the fixing piece 25 in front of the mounting space 26 and then blow out through the air outlet 243 of the fixing-piece assembly portion 24 at the rear side of the mounting space 26. Thus the scents from the fragrance tablet 3 are blown to user's face together with the air flows. Thereby the present device wakes users up and relaxes their minds and bodies.

Figure 5:
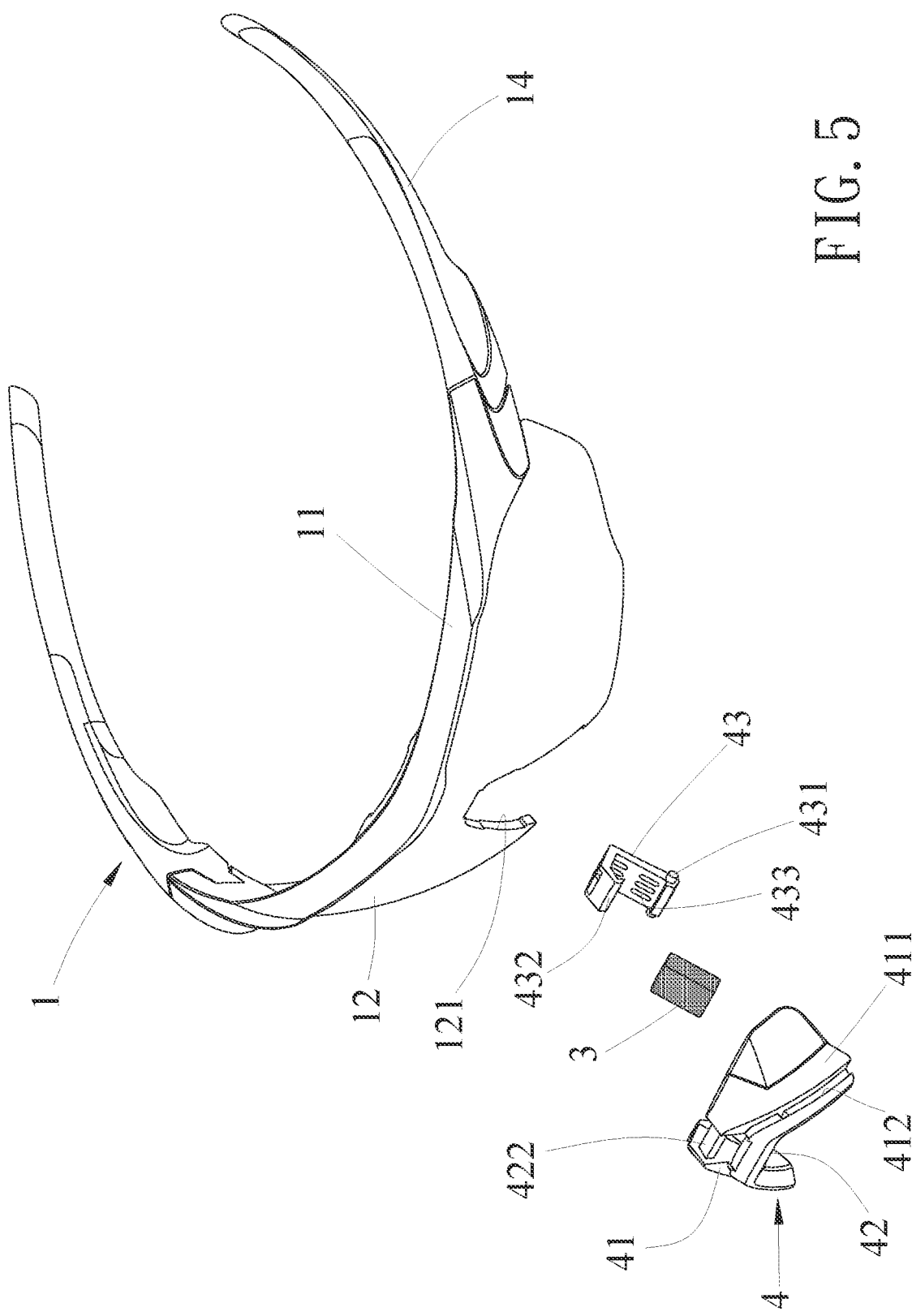
FIG. 5 is an exploded view of an embodiment according to the present invention.
Figure 6:
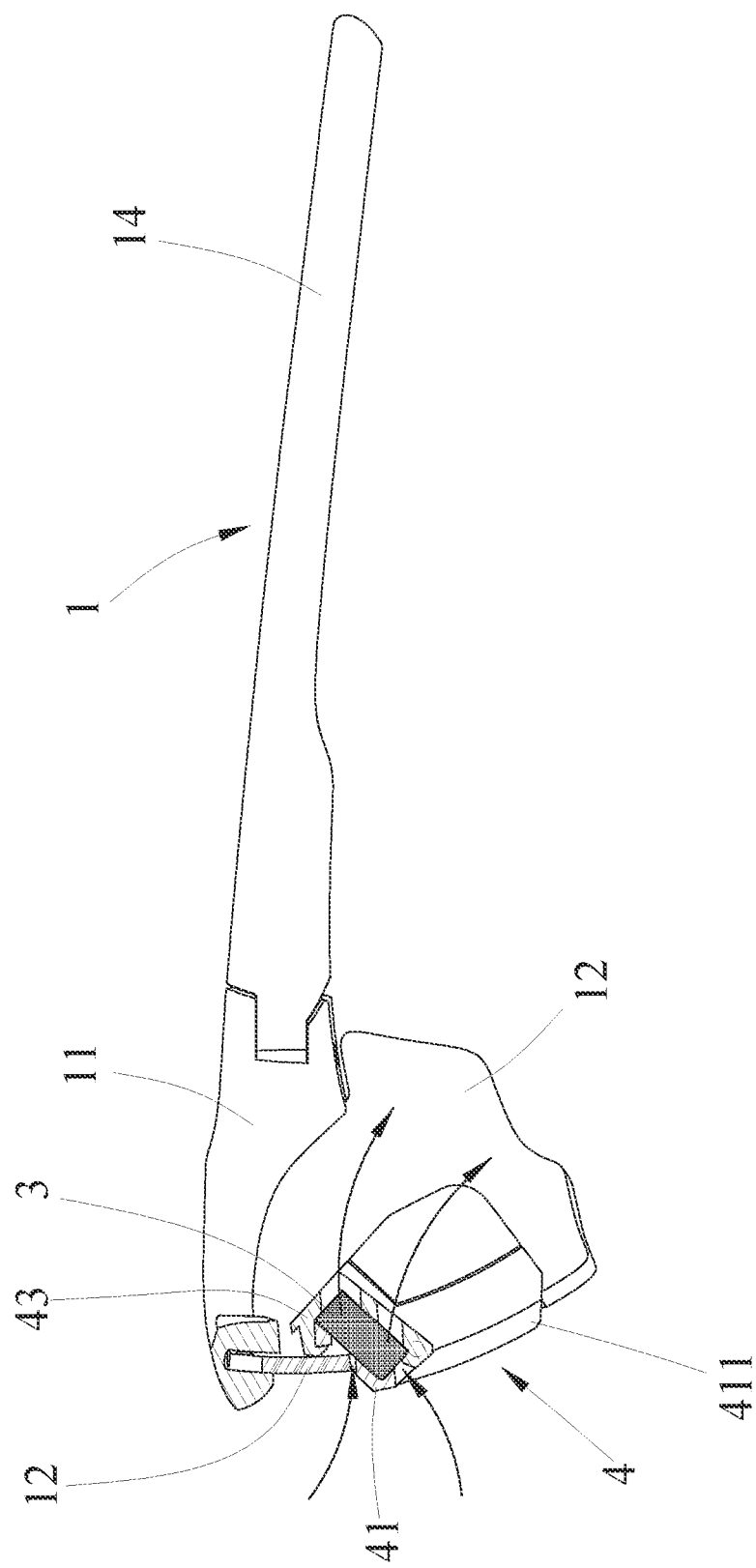
FIG. 6 is a sectional view of another embodiment according to the present invention.

Refer to FIGS. 5-7, another embodiment of the present invention is disclosed. In this embodiment, a nose bridge 4 includes a bridge body 41 which is provided with a wing portion 411 on each of two sides thereof and a mounting slot 412 formed on the wing portion 411 for being mounted and connected to the notch 121 of the lens 12 correspondingly. The nose bridge 4 further includes a fixing-piece assembly portion 42 and a fixing piece 43 located behind the fixing-piece assembly portion 42. The fixing-piece assembly portion 42 is formed between the two wing portions 411 of the bridge body 41 and provided with a pivot hole 421 on each of two sides thereof and a locking bar 422 on an upper end thereof. A pivot pin 431 is disposed on each of two sides of the fixing piece 43 for being pivotally connected to the pivot hole 421 on each of the two sides of the fixing-piece assembly portion 42 while a hook portion 432 is formed on an upper end of the fixing piece 43 for being locked and connected to the locking bar 422 on the upper end of the fixing-piece assembly portion 42. Thus a mounting space 44 is defined by the fixing piece 43 together with the fixing-piece assembly portion 42 on the bridge body 41 and used for mounting the fragrance tablet 3. The fixing-piece assembly portion 42 on the bridge body 41 is provided with at least one air inlet 423 at the position corresponding to the mounting space 44 while the fixing piece 43 is provided with at least air outlet 433 at the position corresponding to the mounting space 44. The air inlet 423 and the air outlet 433 are aligned with each other and communicated with the mounting space 44.

While in use, the hook portion 432 on the upper end of the fixing piece 43 and the locking bar 422 on the upper end of the fixing-piece assembly portion 42 of the nose bridge 4 are released from the locked state and then the fragrance tablet 3 is mounted into the mounting space 44 formed between the fixing-piece assembly portion 42 and the fixing piece 43. Next the hook portion 432 of the fixing piece 43 and the locking bar 422 on the upper end of the fixing-piece assembly portion 42 are locked with each other again for mounting and fixing the fragrance tablet 3 in the mounting space 44. Thereby the nose bridge 4 is fitted on bridge of user's nose by the wing portions 411 on two sides of the nose bridge 4 while the user wearing the present eyeglasses and the fragrance tablet 3 in the nose bridge 4 is just beside and quite close to the user's nose. Thus users can smell scents emanated from the fragrance tablet 3 and thus feel refreshing and even relieve from fatigue. Moreover, the fixing-piece assembly portion 42 and the fixing piece 43 of the nose bridge 4 are provided with the air inlet 423 and the air outlet 433 respectively at the position corresponding to the mounting space 44 for spread of scents of the fragrance tablet 3. When there are air flows created by users who are walking or riding bikes, the air flows bring scents emanated from the fragrance tablet 3 in the mounting space 44 to the user's face under guidance of the air inlet 423 and the air outlet 433 corresponding to the mounting space 44. Thereby users can smell the scents from the fragrance tablet 3 easier.

The above embodiments or figures are not intended to limit the implementation of the present device. The present fragrance tablet 3 which absorbs essential oils emanates scents for refreshing, stress relief, relieving fatigue, eliminating anxiety, preventing motion sickness, etc. so that the present device is capable of being applied to people who always work under high levels of pressure such as athletes, soldiers, coast guard officials, security guards, vehicle drivers, etc. The scents emanated from the fragrance tablet 3 can refresh them and soothe their minds and bodies. Besides the essential oils, the fragrance tablet 3 can also absorb mosquito repellent liquid. Users can replace the fragrance tablet 3 with different functions according to their needs so that the present device is more convenient to use.

Additional advantages and modifications will readily occur to those skilled in the art. Therefore, the invention in its broader aspects is not limited to the specific details, and representative devices shown and described herein. Accordingly, various modifications may be made without departing from the spirit or scope of the general inventive concept as defined by the appended claims and their equivalent.

What is claimed is:
1. A fragrant eyeglass, comprising:
an eyeglass body, the eyeglass body including a frame having a front surface and a rear surface opposite to the front surface, a lens disposed on the frame and provided with a notch formed on a middle portion of a bottom side of the lens, a temple arranged at each of two opposing sides of the frame, and a nose-bridge assembly portion formed at the rear surface of the frame, wherein a positioning piece is formed on each of two opposing sides of the nose-bridge assembly portion, wherein a positioning area is formed between the two opposing positioning pieces, wherein a first locking slot is arranged at an upper end of the positioning area, and wherein a tenon is disposed on a lower end of the positioning area;
a nose bridge disposed on the eyeglass body and provided with a mounting space, at least one air inlet and at least one air outlet are formed in the nose bridge and are in communication with the mounting space, and the nose bridge, further, including:
- a bridge body having a wing portion formed on each of two opposing sides of the bridge body, and a mounting slot formed on each wing potion for being mounted to a corresponding section of the notch of the lens;
- a connection piece formed above the wing portions of the bridge body for being mounted to the positioning area formed on the nose- bridge assembly portion of the frame, and another tenon formed on an upper end of the connection piece for being locked and positioned in the first locking slot formed on the upper end of the nose-bridge assembly portion of the frame; and a limiting piece formed on each of two opposing sides of a front surface of the connection piece, a limit area formed between the opposing limiting pieces, and the two positioning pieces formed on the nose- bridge assembly portion being mounted in the limit area, wherein a second locking slot is formed under the limit area for locking and positioning the tenon on the lower end of the positioning area of the nose-bridge assembly portion;
- a fixing-piece assembly portion formed between the two opposing wing portions of the bridge body, a locking hole formed on a top end of the fixing-piece assembly portion, and a pivot hole formed on each of two opposing sides of the fixing-piece assembly portion; and
- a fixing piece disposed in a front of the fixing-piece assembly portion, a pivot pin formed on each of two opposing sides of the fixing-piece assembly portion for being pivotally connected to a corresponding pivot hole of the fixing-piece assembly portion, and a locking block formed on an upper end of the fixing piece for being locked in the locking hole of the fixing-piece assembly portion;

wherein the mounting space is formed between the fixing piece and the fixing-piece assembly portion; wherein the at least one air inlet is formed on the fixing piece at a position corresponding to the mounting space, and wherein the at least one air outlet is formed on the fixing-piece assembly portion at a position corresponding to the mounting space; and wherein the at least one air inlet and the at least one air outlet are aligned in positional relationship with respect to each other; and at least one fragrance tablet mounted in the mounting space of the nose bridge.

2. A fragrant eyeglass, comprising:

an eyeglass body, the eyeglass body including a frame, a lens disposed on the frame, the lens including a notch formed on a middle portion of a bottom side thereof, and a temple arranged at each of two opposing sides of the frame;

a nose bridge disposed on the eyeglass body and provided with a mounting space, at least one air inlet and at least one air outlet are formed in the nose bridge and are in communication with the mounting space, and the nose bridge, further, including:
- a bridge body having a wing portion formed on each of two opposing sides of the bridge body, and a mounting slot formed on each wing potion for being mounted and connected to a corresponding section of the notch of the lens;
- a fixing-piece assembly portion formed between the two opposing wing portions of the bridge body, a locking bar formed on an upper end of the fixing-piece assembly portion, and a pivot hole formed on each of two opposing sides of the fixing-piece assembly portion; and
- a fixing piece disposed behind the fixing-piece assembly portion, a pivot pin disposed on each of two opposing sides of the fixing piece for being pivotally connected to a corresponding one of the pivot holes on the two opposing sides of the fixing-piece assembly portion, and a hook portion formed on an upper end of the fixing piece for being locked to the locking bar on the upper end of the fixing-piece assembly portion;

wherein the mounting space is formed between the fixing piece and the fixing-piece assembly portion; wherein the at least one air inlet is formed on the fixing-piece assembly portion at a position corresponding to the mounting space and the at least one air outlet is formed on the fixing piece at a position corresponding to the mounting space; and wherein the at least one air inlet and the at least one air outlet are aligned in positional relationship with respect to each other; and at least one fragrance tablet mounted in the mounting space of the nose bridge.

\* \* \* \* \*